United States Patent
Truong et al.

(10) Patent No.: US 10,371,559 B2
(45) Date of Patent: Aug. 6, 2019

(54) DIFFERENTIAL SPECTRAL LIQUID LEVEL SENSOR

(71) Applicant: The Boeing Company, Chicago, IL (US)

(72) Inventors: Tuong K. Truong, Bellevue, WA (US); Eric Y. Chan, Mercer Island, WA (US); Dennis G. Koshinz, Bellevue, WA (US); Kim Quan Anh Nguyen, Seattle, WA (US); Eric J. Harvey, Everett, WA (US)

(73) Assignee: The Boeing Company, Chicago, IL (US)

( * ) Notice: Subject to any disclaimer, the term of this patent is extended or adjusted under 35 U.S.C. 154(b) by 87 days.

(21) Appl. No.: 15/488,932

(22) Filed: Apr. 17, 2017

(65) Prior Publication Data

US 2018/0299317 A1      Oct. 18, 2018

(51) Int. Cl.
*G01F 23/292* (2006.01)
*G01N 9/00* (2006.01)
*G01N 9/36* (2006.01)

(52) U.S. Cl.
CPC ........... *G01F 23/2925* (2013.01); *G01N 9/00* (2013.01); *G01N 9/36* (2013.01)

(58) Field of Classification Search
CPC ................................ G01F 23/292; G01N 9/24
See application file for complete search history.

(56) References Cited

U.S. PATENT DOCUMENTS 4,274,705 A * 6/1981 Miller ................. G01F 23/2927
                                                        385/12
4,727,247 A * 2/1988 Johnston ................ G01B 11/02
                                                        250/227.23

(Continued)

FOREIGN PATENT DOCUMENTS

CA      1332205      10/1994
DE      3940455 A1   9/1990

(Continued)

OTHER PUBLICATIONS

OSP Fiber Optic Transmission Systems. (n.d.). Retrieved Apr. 21, 2016, from http://www.thefoa.org/tech/ref/appln/OSPdatalink.html.*

(Continued)

*Primary Examiner* — Peter J Macchiarolo
*Assistant Examiner* — Alexander A Mercado
(74) *Attorney, Agent, or Firm* — Ostrager Chong Flaherty & Broitman P.C.

(57) ABSTRACT

Systems and methods that use a differential spectral liquid level sensor to measure the level of liquid in a reservoir (e.g., a fuel tank or other storage container). The use of a differential spectral liquid level sensor solves the problem of common-mode intensity variations (i.e., intensity variations not due to the level of the liquid) by having two different wavelengths propagate through the same optical path but have different spectral attenuations in the liquid. By determining the ratio of the received optical powers, common-mode intensity variations can be neutralized, thereby enhancing the accuracy of the received power reading and the resulting liquid level indication.

11 Claims, 9 Drawing Sheets

(56) References Cited

U.S. PATENT DOCUMENTS

| | | | |
|---|---|---|---|
| 4,839,515 A * | 6/1989 | Kershaw | G01D 5/268 250/201.1 |
| 4,861,727 A * | 8/1989 | Hauenstein | A61B 5/1459 436/136 |
| 4,870,292 A | 9/1989 | Alpert et al. | |
| 4,880,971 A * | 11/1989 | Danisch | G01F 23/292 340/619 |
| 4,928,006 A | 5/1990 | Kershaw | |
| 4,942,306 A | 7/1990 | Colbourne | |
| 4,950,885 A * | 8/1990 | Kershaw | G01D 5/268 250/227.25 |
| 4,994,682 A | 2/1991 | Woodside | |
| 6,172,377 B1 | 1/2001 | Weiss | |
| 6,274,880 B1 | 8/2001 | Walker | |
| 6,333,512 B1 | 12/2001 | Wirthlin | |
| 6,429,447 B1 | 8/2002 | Nowak et al. | |
| 6,795,598 B1 | 9/2004 | Devenyi | |
| 6,801,678 B2 * | 10/2004 | Murshid | G01F 23/292 250/227.14 |
| 6,831,290 B2 * | 12/2004 | Mentzer | G01F 23/292 250/227.14 |
| 7,049,622 B1 | 5/2006 | Weiss | |
| 7,161,165 B2 | 1/2007 | Wirthlin | |
| 7,259,384 B2 * | 8/2007 | Hariram | G01F 23/706 250/573 |
| 7,573,565 B1 * | 8/2009 | Mentzer | G01K 11/125 285/13 |
| 7,660,494 B2 | 2/2010 | Anderson | |
| 7,710,567 B1 | 5/2010 | Mentzer et al. | |
| 9,228,956 B2 * | 1/2016 | Weling | G01N 21/3577 |
| 2001/0022342 A1 * | 9/2001 | Wirthlin | G01C 9/06 250/229 |
| 2003/0053064 A1 * | 3/2003 | Nishimura | G01J 9/00 356/414 |
| 2004/0021100 A1 * | 2/2004 | Gouzman | G01F 23/2927 250/573 |
| 2004/0156038 A1 * | 8/2004 | Cao | G01J 1/4257 356/73.1 |
| 2005/0236591 A1 | 10/2005 | Wirthlin | |
| 2007/0100580 A1 * | 5/2007 | Marcus | G01B 11/0683 702/170 |
| 2007/0145309 A1 | 6/2007 | Zhang | |
| 2009/0076744 A1 | 3/2009 | Anderson | |
| 2009/0084995 A1 | 4/2009 | Cierullies et al. | |
| 2010/0202726 A1 * | 8/2010 | Egalon | G01F 23/2927 385/12 |
| 2014/0014777 A1 | 1/2014 | Kreitmair-Steck et al. | |
| 2015/0100253 A1 * | 4/2015 | Austerlitz | G01F 22/00 702/55 |
| 2016/0138958 A1 * | 5/2016 | Truong | G01F 23/292 250/227.28 |
| 2016/0139036 A1 * | 5/2016 | Babin | G01N 21/255 356/408 |
| 2018/0299317 A1 * | 10/2018 | Truong | G01F 23/2925 |

FOREIGN PATENT DOCUMENTS

| | | |
|---|---|---|
| GB | 2293007 A | 3/1996 |
| WO | 2010051806 A1 | 5/2010 |

OTHER PUBLICATIONS

Abstract, Zhao et al., "Novel light-leaking optical fiber liquid-level sensor for aircraft fuel gauging", Opt. Eng., vol. 52, No. 1, 014402 (Jan. 4, 2013); http://dx.doi.org/10.1117/1.OE.52.1.014402.
English Abstract of DE3940455.

* cited by examiner

DIFFERENTIAL SPECTRAL LIQUID LEVEL SENSOR

BACKGROUND

This disclosure generally relates to systems and methods for measuring a level of liquid in a reservoir, such as a storage tank or other container. More particularly, this disclosure relates to systems and methods for liquid level measurement using an optical sensor.

The level of a liquid is continuously measured in many commercial and military applications. For example, liquid-level sensors are commonly used in the fuel tanks of aircraft, automobiles, and trucks. Liquid-level sensors are also used to monitor liquid levels within storage tanks used for fuel dispensing, wastewater treatment, chemical storage, food processing, etc.

Many transducers for measuring liquid level employ electricity. The electrical output of such transducers changes in response to a change in the liquid level being measured, and is typically in the form of a change in resistance, capacitance, current flow, magnetic field, frequency, and so on. These types of transducers may include variable capacitors or resistors, optical components, Hall Effect sensors, strain gauges, ultrasonic devices, and so on.

Currently most fuel sensors on aircraft use electricity. For example, existing electrical capacitance sensors require electrical wiring inside the tank, which in turn requires complex installations and protection measures to preclude a safety issue under certain electrical fault conditions. This electrical wiring requires careful shielding, bonding, and grounding to minimize stray capacitance and further requires periodic maintenance to ensure electrical contact integrity.

A simplex (non-differential) optical impedance fuel level sensor based on optical intensity measurement has been proposed which would eliminate all electrical elements. One such optical impedance fuel level sensor comprises two optical fibers spaced apart inside a meniscus tube: a side-emitting optical fiber that transmits light along its length and a side-receiving optical fiber that receives emitted light along its length. The meniscus tube minimizes the sloshing of fuel level. The variable fuel level in the tank produces changes in the optical impedance between the two optical fibers, resulting in changes in the total light received by an optical detector.

However, the aforementioned simplex optical impedance fuel level sensor is susceptible to inaccuracy due to intensity variations along the optical path that are not related to fuel level. These intensity variations may be attributable to one or more of the following factors: (1) temperature variation; (2) surface tension wetting (non-shedding of liquid); (3) fuel gunk buildup on the optical window surface of the fiber sensor elements; (4) ice slush in the lower portion of the fuel tank due to water condensation and cold temperature; (5) fuel surface tilt in a dynamic flight environment; (6) fiber attenuation due to aging; (7) fiber attenuation due to bending; (8) connector attenuation due to alignment; (9) non-uniformity of light emitting along the length of the side-emitting optical fiber due to manufacturing imperfection; and (10) non-uniformity of light received along the length of the side-receiving optical fiber due to manufacturing imperfection.

It would be desirable to provide a liquid level sensor that measures the optical impedance of light propagating through the liquid in a manner that is not corrupted by one or more of the aforementioned sources of intensity variation.

SUMMARY

The subject matter disclosed herein is directed to improvements in systems and methods that use an optical impedance sensor to measure the level of liquid in a reservoir (e.g., a fuel tank or other storage container). More specifically, various embodiments of a differential spectral liquid level sensor disclosed below solve the problem of common-mode intensity variations by having two different wavelengths propagate through the same optical path but have different spectral attenuations in the liquid. By determining the ratio of the received optical powers, common-mode intensity variations can be neutralized, thereby enhancing the accuracy of the received power reading and the resulting liquid level indication.

In accordance with some embodiments disclosed in some detail below, a differential spectral fuel level sensor is provided that employs light of two different wavelengths that both travel the same optical path through a column of fuel in a fuel tank. The light of two wavelengths is optically coupled into a side-emitting optical fiber disposed vertically in the fuel tank. The side-emitting optical fiber emits some of the received light along its length toward a side-receiving optical fiber, also disposed vertically inside the fuel tank. The side-emitting and side-receiving optical fibers are spaced apart inside a meniscus tube. The meniscus tube minimizes the sloshing of fuel level. The variable fuel level in the fuel tank produces changes in the optical impedance between the two optical fibers, resulting in changes in the total light received by any optical detector optically coupled to the side-emitting optical fiber. Some of the light received along the length of the side-receiving optical fiber exits the upper end of the side-receiving optical fiber and is optically coupled to a differential receiver. In accordance with one embodiment, the differential receiver comprises a pair of optical filters and an associated pair of optical detectors. In accordance with another embodiment, the differential receiver comprises a dichroic mirror and a pair of optical detectors. For the same differential spectral sensing functionality, one broadband optical source can be used in place of two different optical sources, or one optical detector can be used in place of a differential receiver by time-division multiplexing of the two different wavelength sources. (The terms "optical source" and "light source", as used in this disclosure, are synonymous.) Since the fuel level measurement is based on optical intensity, many other intensity variations that are not related to fuel level can affect the received optical power and therefore create error in fuel level measurement. These other (i.e., common-mode) intensity variations may include temperature, component aging, fuel gunk deposit on the sensor elements, etc. By using differential wavelengths, the ratio of the received optical powers can be calculated, which ratio neutralizes intensity variations that are not due to fuel level.

Although various embodiments of systems and methods for optically measuring the level of fuel in a fuel tank will be described in some detail below, one or more of those embodiments may be characterized by one or more of the following aspects.

One aspect of the subject matter disclosed in detail below is a system for measuring a level of liquid in a reservoir, comprising: one optical source which alone or two optical sources which collectively outputs light comprising a first wavelength and light comprising a second wavelength different than the first wavelength; a side-emitting optical fiber optically coupled to the one or two optical source(s); a side-receiving optical fiber that is positioned parallel to and at a distance from the side-emitting optical fiber; and a differential receiver optically coupled to the side-receiving optical fiber and configured to convert light having the first wavelength into first electrical signals and convert light having the second wavelength into second electrical signals. The light comprising a first wavelength and the light comprising a second wavelength have different attenuations when propagating through the liquid.

In accordance with some embodiments, the system further comprises a computer system configured to calculate an estimated level of liquid in the reservoir based on a difference of the first and second electrical signals output by the differential receiver. In addition, the system may further comprise a display device electrically coupled to the computing system, in which case the computing system is further configured to execute the following operations: storing data representing a geometry of the reservoir; receiving data representing a measurement of a density of the liquid in the reservoir; calculating a mass of liquid remaining in the reservoir based on the geometry of the reservoir, the density of the liquid and the estimated level of liquid; and outputting an electrical signal representing the calculated mass of liquid in the reservoir to the display device.

In accordance with one embodiment, the differential receiver comprises: a first optical filter that passes light having the first wavelength, but does not pass light having the second wavelength; a first optical detector that receives light that has passed through the first optical filter; a second optical filter that passes light having the second wavelength, but does not pass light having the first wavelength; and a second optical detector that receives light that has passed through the second optical filter. In accordance with another embodiment, the differential receiver comprises: a dichroic mirror that passes light having the first wavelength and reflects light having the second wavelength; a first optical detector positioned to receive light passed by the dichroic mirror; and a second optical detector positioned to receive light reflected by the dichroic mirror.

Another aspect of the subject matter disclosed in detail below is a system for measuring a level of liquid in a reservoir, comprising: a first optical source that outputs light comprising a first wavelength; a second optical source that outputs light comprising a second wavelength different than the first wavelength; a time-division multiplexing controller configured to control the first and second optical sources to output time-division multiplexed optical pulses having the first and second wavelengths in alternating sequence; a side-emitting optical fiber that is optically coupled to the first and second optical sources; a side-receiving optical fiber that is positioned parallel to and at a distance from the side-emitting optical fiber; an optical detector that is optically coupled to receive light from the side-receiving optical fiber and convert the received light to electrical signals; and a time-division demultiplexer that is electrically coupled to the optical detector and comprises switches which are controlled to demultiplex the electrical signals output by the optical detector. In accordance with some embodiments, the system further comprises a computer system configured to calculate an estimated level of liquid in the reservoir based on a difference of the demultiplexed signals output from the time-division demultiplexer.

A further aspect of the subject matter disclosed in detail below is a method for measuring a height of liquid in a reservoir, comprising: placing a side-emitting optical fiber and a side-receiving optical fiber in the reservoir having respective locations whereat the side-emitting optical fiber and side-receiving optical fiber are mutually parallel and separated by a distance; outputting light comprising a first wavelength and light comprising a second wavelength different than the first wavelength from a single broadband optical source or from respective optical sources, wherein the light comprising a first wavelength and the light comprising a second wavelength have different attenuations when propagating through the liquid; guiding the light comprising the first and second wavelengths into the side-emitting optical fiber; side-emitting at least some of the light received by the side-emitting optical fiber toward the side-receiving optical fiber; guiding at least some of the light comprising the first wavelength received by the side-receiving optical fiber onto a first optical detector; guiding at least some of the light comprising the second wavelength received by the side-receiving optical fiber onto a second optical detector; converting light having the first wavelength that impinges on the first optical detector into first electrical signals; converting light having the second wavelength that impinges on the second optical detector into second electrical signals; calculating an estimated level of liquid in the reservoir based on a difference of the first and second electrical signals; and displaying a fuel gauge that indicates the estimated level of liquid.

Yet another aspect is a method for measuring a height of liquid in a reservoir, comprising: placing a side-emitting optical fiber and a side-receiving optical fiber in the reservoir having respective locations whereat the side-emitting optical fiber and side-receiving optical fiber are mutually parallel and separated by a distance; guiding a series of time-division-multiplexed optical pulses into one end of the side-emitting optical fiber, wherein the time-division-multiplexed optical pulses comprise alternating optical pulses having the first and second wavelengths respectively; side-emitting at least some of the optical pulses received by the side-emitting optical fiber toward the side-receiving optical fiber; guiding at least some of the time-division-multiplexed optical pulses received and output by the side-receiving optical fiber onto an optical detector; converting time-division-multiplexed optical pulses that impinge on the optical detector into time-division-multiplexed electrical signals; demultiplexing the time-division-multiplexed electrical signals output by the optical detector to generate first and second electrical signals; and calculating an estimated level of liquid in the reservoir based on a difference of the first and second electrical signals.

In accordance with some embodiments, each of the methods briefly described in the preceding two paragraphs further comprises: storing data representing a geometry of the reservoir; measuring a density of the liquid in the reservoir; calculating a mass of liquid remaining in the reservoir based on the geometry of the reservoir, the density of the liquid and the estimated level of liquid; and displaying a gauge that indicates the calculated mass of liquid in the reservoir.

Other aspects of differential spectral liquid level sensors suitable for use in reservoirs are disclosed and claimed below.

BRIEF DESCRIPTION OF THE DRAWINGS

The features, functions and advantages discussed in the preceding section can be achieved independently in various embodiments or may be combined in yet other embodiments. Various embodiments will be hereinafter described with reference to drawings for the purpose of illustrating the above-described and other aspects.

Reference will hereinafter be made to the drawings in which similar elements in different drawings bear the same reference numerals.

DETAILED DESCRIPTION

Various embodiments of systems and methods for optical measurement of a level of liquid in a reservoir will now be described in detail for the purpose of illustration. At least some of the details disclosed below relate to optional features or aspects, which in some applications may be omitted without departing from the scope of the claims appended hereto. The disclosed optical impedance fuel level sensor has application in the measurement of the liquid level in a fuel tank of a vehicle (such as an airplane) or in other types of liquid storage containers, including standing structures. Fuel tanks and other liquid storage containers are collectively referred to herein as "reservoirs".

In particular, illustrative embodiments of an optical impedance fuel level sensor on an airplane are described in some detail below. However, not all features of an actual implementation are described in this specification. A person skilled in the art will appreciate that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
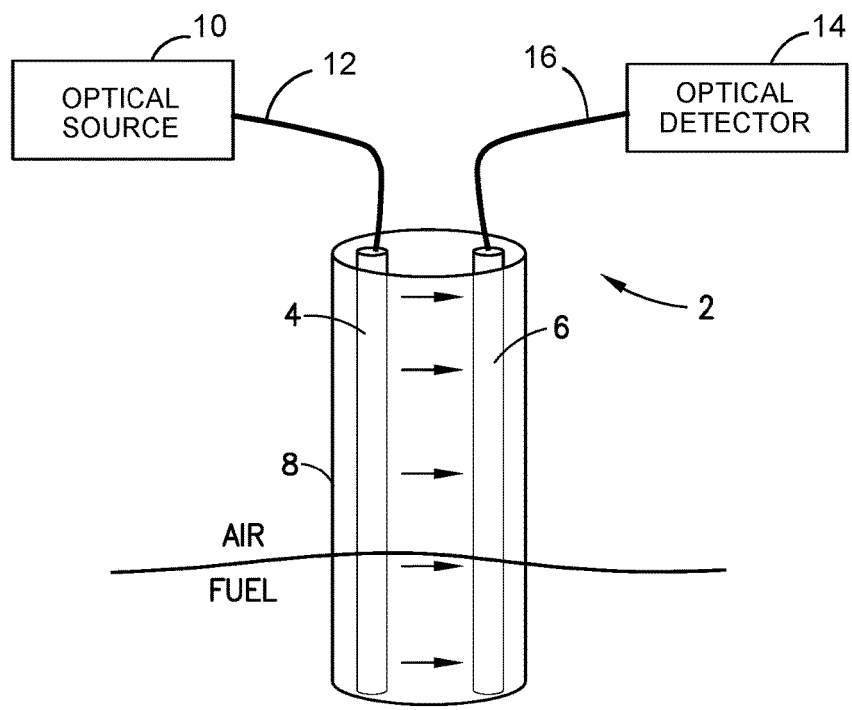
FIG. 1 is a hybrid diagram representing a system for measuring a level of a liquid comprising an optical impedance sensor that detects modulations in the optical impedance of the liquid. This hybrid diagram comprises a block diagram showing components of an optical transceiver and a diagram representing an isometric view of the optical impedance sensor. The nonlinear line spanning the sensor represents a level of liquid; the arrows represent photons propagating from one optical fiber to another optical fiber.

FIG. 1 is a hybrid diagram representing a system for measuring a level of fuel in a reservoir in accordance with the optical impedance modulation concept. The system depicted in FIG. 1 comprises an optical impedance sensor 2 that detects the optical impedance of the fluid separating a side-emitting optical fiber 4 and a side-receiving optical fiber 6, obtaining optical power data that can be later used to determine the fuel level. In accordance with the embodiment shown in FIG. 2, the side-emitting optical fiber 4 is optically coupled to an optical source 10 (e.g., a laser or a light-emitting diode (LED)) by means of an optical fiber 12; and the side-receiving optical fiber 6 is optically coupled to an optical detector 14 (e.g., a photodiode) by means of an optical fiber 16.

The optical impedance sensor 2 further comprises a meniscus tube 8 that minimizes fuel sloshing in a fuel tank (not shown). The nonlinear line spanning the optical impedance sensor 2 in FIG. 1 represents a level of fuel. The side-emitting and side-receiving optical fibers 4 and 6 are placed inside the meniscus tube 8 in spaced-apart relationship (preferably the fibers are straight and parallel to each other). In cases where the fuel tank is incorporated in a wing of an airplane, the side-emitting and side-receiving optical fibers 4 and 6 are preferably rigidly supported in a fixed spatial relationship to provide a separation distance d which is optimized for optical received power versus ice slush particles that may form in the fuel tank. The meniscus tube 8, which extends to the floor of the fuel tank, has openings near that floor which allow fuel to flow into the volume of space bounded by the meniscus tube 8. The level of the fuel will be the same inside and outside the meniscus tube 8.

When pumped by the optical source 10, the side-emitting optical fiber 4 emits light radially outward and toward the side-receiving optical fiber 6. The axial distribution of emitted light may be substantially constant along the length of side-emitting optical fiber 4. A first portion of the light will pass through the fuel and illuminates a lower portion of the side-receiving optical fiber 6. A second portion of light emitted by side-emitting optical fiber 4 will pass through the air and illuminate an upper portion of the side-receiving optical fiber 6. At least some of the light received by side-receiving optical fiber 6 is guided upwards and other light is guided downwards inside the core of side-receiving optical fiber 6. The light guided downwards may be reflected upwards from a mirror (not shown in FIG. 1, but see mirror 18 in FIG. 9) disposed at the bottom end of side-receiving optical fiber 6. The light is guided upwards and exits the upper end of side-receiving optical fiber 6. The light output by side-receiving optical fiber 6 is guided by optical fiber 16 to the optical detector 14, which converts impinging light into electrical current. This electrical current is conducted by a cable to a computer or processor (not shown in FIG. 1). The computer or processor is configured to analyze the optical power data acquired from the optical detector 14 and compute the height h of the air/fuel interface. As will be explained in more detail below, the computer or processor may also be configured to receive fuel temperature data from a temperature sensor and fuel density data from a densitometer and compute the quantity of fuel in the fuel tank based on the optical power, fuel density data and geometry of the fuel tank (or compartment thereof). In this case, the computer may be referred to as a fuel quantity processing unit (FQPU).

The arrows in FIG. 1 represent light (i.e., photons) propagating from the side-emitting optical fiber 4 to the side-receiving optical fiber 6 during operation of optical source 10. During monitoring of the fuel level, the brightness (i.e., intensity) of the light produced by optical source 10 (i.e., its optical power) is preferably constant. As the fuel level varies, the optical impedance of the fuel in the volume of space between side-emitting optical fiber 4 and side-receiving optical fiber 6 changes in dependence on the fuel level, due to the fact that air and fuel have different refractive indices.

It is well known that air has an index of refraction less than the index of refraction of fuel; that fuel has an index of refraction less than the index of refraction of cladding of an optical fiber; and that the cladding has an index of refraction less than the index of refraction of the core of the optical fiber. The refractive indices determine the amount of light that is reflected when reaching an interface.

Since more optical power is lost (i.e., optical impedance is greater) in liquids than in air, the optical power output by the side-receiving optical fiber 6 will monotonically increase as the liquid level falls. In other words, as the fuel level changes, the optical impedance between side-emitting optical fiber 4 and side-receiving optical fiber 6 will change. These changes in optical impedance in turn produce changes in the optical power (i.e., light intensity) output by the side-receiving optical fiber 6 to the optical detector 14.

Although not depicted in FIG. 1, each optical fiber is a flexible, optically transparent or translucent fiber made of extruded glass or plastic. It can function as a waveguide or light pipe to transmit light between the two ends of the fiber. The term "optical fiber" as used herein refers to a cylindrical dielectric waveguide that transmits light along its axis. The fiber consists of a transparent core surrounded by a transparent cladding layer (hereinafter "cladding"), both of which are made of dielectric materials. Light is kept in the core by the phenomenon of total internal reflection. To confine the optical signal in the core, the refractive index of the core is greater than that of the cladding. The boundary between the core and cladding may either be abrupt, as in step-index fiber, or gradual, as in graded-index fiber. The embodiments disclosed herein employ plastic optical fibers. Plastic optical fibers have high transmission capacity, excellent immunity to electro-magnetic interference-induced noise, light weight, high mechanical strength, and outstanding flexibility. Plastic optical fibers are also larger in diameter as compared to glass optical fibers. Due to their larger diameters, plastic optical fibers have greater tolerance for fiber misalignment than glass optical fibers have. Because of this large misalignment tolerance, plastic optical fiber-based networks have lower maintenance and installation costs. In aerospace platforms, plastic optical fibers also greatly reduce the cost of connectors and transceiver components used in an avionics network. In alternative embodiments, glass optical fibers can be used in place of plastic optical fibers.

The systems and methods disclosed herein also utilize side-emitting optical fibers. The side-emitting optical fibers utilized herein have a plastic or glass core clad with a material that is different than the material of the core. To enable side emission, scattering features are introduced into the optical fiber at various locations. In accordance with one method, the core region is doped with small refractive and/or reflective light-scattering particles during manufacture. Alternatively, the surface of the core is modified or treated to have surface features that scatter light out of the core. Some examples of light-emitting surface features include serrations, notches, scratches, texture, roughness, corrugations, etching, abrasion, etc. The entire length of fiber can be modified or treated to have side-emitting properties, or just a portion of the fiber (i.e., a portion along the length or circumference of the fiber, or both). Side-emitting optical fibers also inherently function in reverse, i.e., as "side-receiving" optical fibers, because the same features that scatter light out of the optical fiber (i.e., when illuminated from one end) can also scatter light into the optical fiber (i.e., when illuminated from the side). However, although in theory a side-emitting optical fiber also qualifies as a side-receiving optical fiber, as used herein the term "side-emitting optical fiber" will be used to refer to an optical fiber that receives light at one end and emits at least some of that light from the side, while the term "side-receiving optical fiber" will be used to refer to an optical fiber that receives light from the side and emits at least some of that light from one end.

In accordance with the embodiments disclosed herein, the cladding of the side-emitting optical fiber 4 is modified (e.g., by roughening or notching the circumferential surface) to enable a controlled level of radial light output along the fiber's length. More specifically, the cladding of side-emitting optical fiber 4 may be treated to produce a non-uniform surface at least in an area bounded by a longitudinal slot in a jacket. For example, the outer surface of the cladding may be roughened or notched at least in an area overlapped by a longitudinal slot in a jacket, thereby forming a side window, as will be described in more detail below with reference to FIGS. 10 and 11. The cladding of the side-receiving optical fiber 6 may be modified in a similar manner to form a side window that faces toward the side window of the side-emitting optical fiber 4 when the optical sensor is installed inside a fuel tank.

In addition or in the alternative, the side-receiving optical fiber 6 can be a fluorescent fiber having a core containing fluorescing dopants, which can be activated by light from the side-emitting optical fiber 4 impinging on the side window of the side-receiving optical fiber 6 and then entering the core of the side-receiving optical fiber 6. (Fluorescence occurs when an orbital electron relaxes to its ground state by emitting a photon of light after being excited to a higher quantum state by some type of energy.) The fluorescing dopants produce light which travels along the length of the side-receiving optical fiber 6 and is then output to the optical detector 14.

At any given axial position along the length of the side-emitting optical fiber 4, the circumferential variation in the emitted light is preferably strongly peaked in a narrow angular range subtended by the side window formed by modification of the cladding of the side-emitting optical fiber 4. As previously mentioned, this side window can be formed by modifying the cladding of the optical fibers (e.g., by notching, scratching or sanding) on only one side to more easily emit light with an angular spread that impinges on a corresponding side window formed by modification of the cladding of the side-receiving optical fiber 6.

Figure 2:
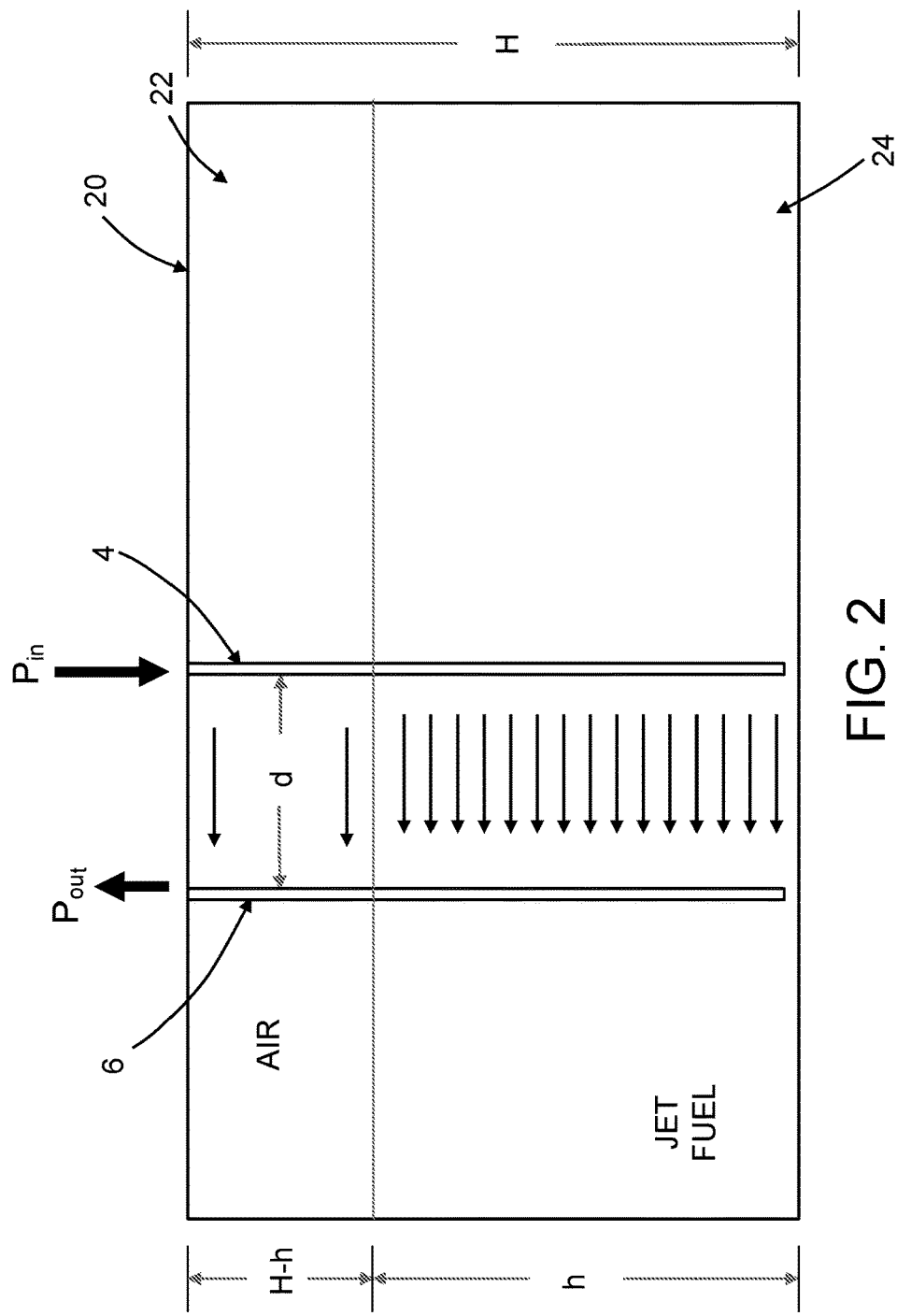
FIG. 2 is a diagram representing a side-emitting optical fiber and a side-receiving optical fiber separated by a distance d inside a fuel tank.

The theoretical underpinning of the optical impedance fuel level sensor concept will now be described with reference to FIG. 2, which shows a side-emitting optical fiber 4 and a side-receiving optical fiber 6 separated by a distance d inside a fuel tank 20 that is partly filled with fuel 24. A typical diameter of side-emitting optical fiber 4 and side-receiving optical fiber 6 is 1 mm. In the configuration depicted in FIG. 2, light from a light source (not shown), having an input optical power $P_{in}$, is input to the side-emitting optical fiber 4. The horizontal arrows in FIG. 2 represent the propagation of side-emitted light from side-emitting optical fiber 4. The light output from the side-receiving optical fiber 6 has an output optical power $P_{out}$ that is highest when the fuel tank 20 is empty. As the fuel level rises, the output optical power $P_{out}$ decreases. By measuring the change in $P_{out}$, the fuel level change can be derived.

In the example shown in FIG. 2, optical fibers are used to measure the level of fuel in a fuel tank. In other embodiments, the same apparatus may be used to detect other liquids. For example, the system described above may be used to detect the presence of water in a container or hydraulic fluids in a reservoir for a hydraulic system. The illustration of detecting fuel in a fuel tank is presented for purposes of illustration and not meant to limit the manner in which the system shown in FIG. 2 may be used.

In FIG. 2, the following dimensions are indicated: the fuel level is h; and the total length of the side-emitting optical fiber 4 and of the side-receiving optical fiber 6 is set equal to H, since the end faces of the two optical fibers are close to the bottom of the fuel tank 20 and H is close to the height of the fuel tank 20. The relationship of output optical power $P_{out}$ versus fuel level h is a function of the side-emitting efficiency per unit area of the side-emitting optical fiber 4, the photo response efficiency per unit area of the side-receiving optical fiber 6, and other factors. Physically, as the fuel level changes, $P_{out}$ is the summation of the output optical power $P_{out/air}$ due to absorption of photons from the side-emitting optical fiber 4 by the air 22 and the output optical power $P_{out/fuel}$ due to absorption of photons from the side-emitting optical fiber 4 by the fuel 24, i.e., $P_{out}=P_{out/air}+P_{out/fuel}$.

In principle, a single side-emitting optical fiber 4 and a single side-receiving optical fiber 6 should be able to provide the fuel level information based on the detected output optical power $P_{out}$ of the side-receiving optical fiber 6. But in a real airplane fuel tank, there are issues of fuel gunk and residue which can build up on the surfaces of the side-emitting optical fiber and side-receiving optical fiber. This build-up obscures the fuel level (h) measuring accuracy. Another consideration is that the quality of fuel used in an airplane in service can change over time because different countries may provide different grades of fuel at their airports. In addition, the sensor system should have a stable light source (laser or LED) to provide a proper optical power input $P_{in}$ to the side-emitting optical fiber 4 for measuring fuel level h. Also, over time the optical fibers can age and the side-emitting optical fiber emitting efficiency and the side-receiving optical fiber response efficiency can be degraded over time.

To overcome these issues, differential spectral fuel level sensors can be installed in a fuel tank which operate by causing light having two different wavelengths to propagate along the same optical path in the fuel. More specifically, two different narrow wavelength ranges having respective center wavelengths which have different spectral attenuations in the fuel are selected. By computing a ratio of the received optical powers of the respective wavelengths, the intensity variations that affect the received power reading and therefore the fuel level accuracy can be neutralized.

Figure 3:
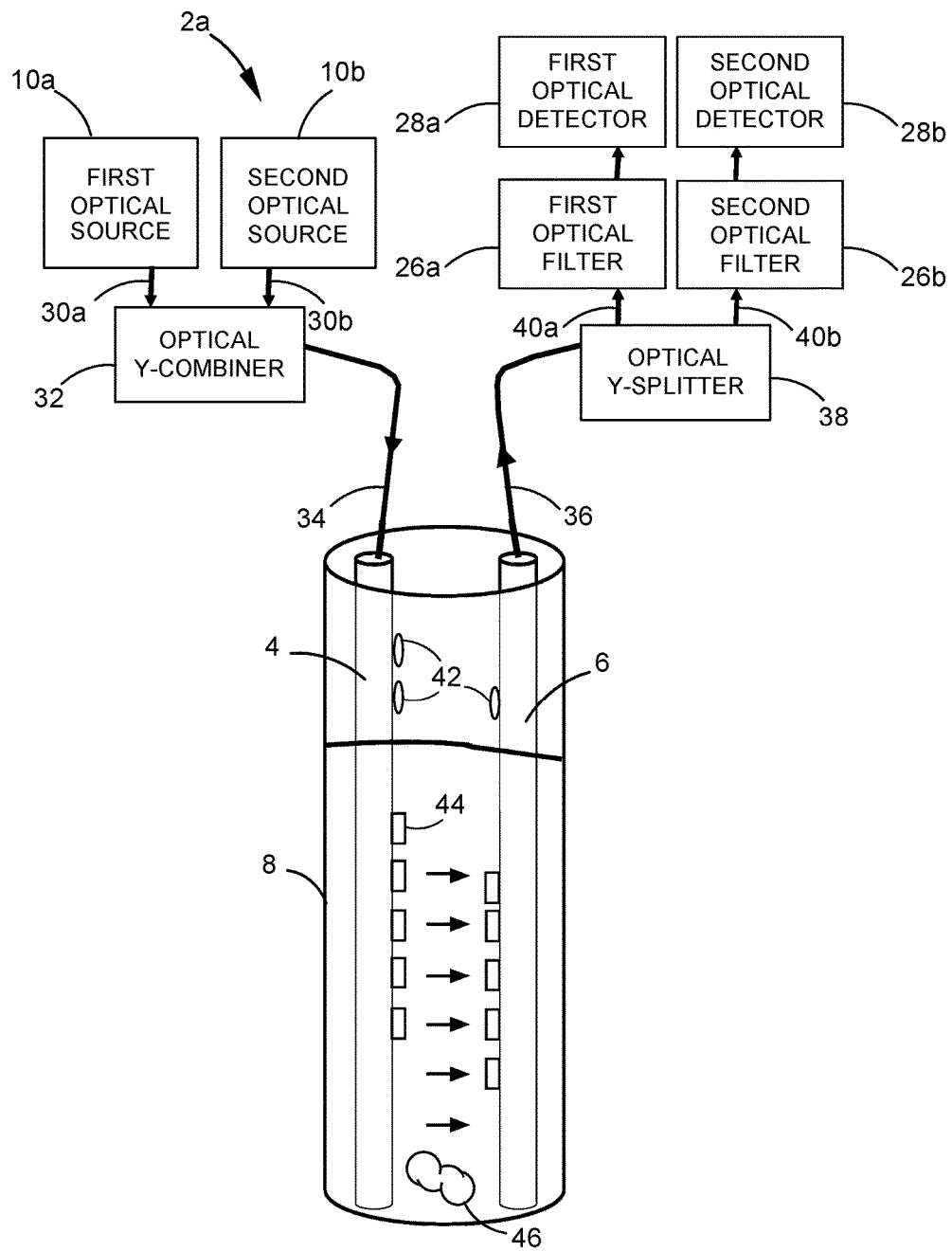
FIG. 3 is a hybrid diagram representing some components of a differential spectral liquid level sensor comprising a pair of differential optical sources and a pair of differential optical detectors in accordance with a first embodiment.

FIG. 3 is a hybrid diagram representing some components of a differential spectral liquid level sensor 2a in accordance with a first example embodiment. FIG. 3 depicts some of the factors which may cause variations in the optical intensity of the light propagating from the side-emitting optical fiber 4 into the side-receiving optical fiber 6, such as surface tension wetting 42 (non-shedding of liquid), fuel gunk buildup 44 on the optical window surface of the fiber sensor elements, and ice slush 46 in the lower portion of the fuel tank due to water condensation and cold temperature.

The differential spectral liquid level sensor 2a depicted in FIG. 3 comprises at least the following components: a first optical source 10a that outputs light comprising a first wavelength; a second optical source 10b that outputs light comprising a second wavelength different than the first wavelength; a side-emitting optical fiber 4 that is optically coupled to the first and second optical sources; a first optical filter 26a that passes light having the first wavelength, but does not pass light having the second wavelength; a first optical detector 28a that receives light that has passed through the first optical filter 26a; a second optical filter 26b that passes light having the second wavelength, but does not pass light having the first wavelength; a second optical detector 28b that receives light that has passed through the second optical filter 26b; and a side-receiving optical fiber 6 that is optically coupled to the first and second optical detectors by way of the first and second optical filters respectively. The first and second optical detectors 28a and 28b convert impinging light into first and second electrical signals respectively. The first and second optical filters 26a and 26b and first and second optical detectors 28a and 28b form a differential receiver that outputs the first and second electrical signals to a computer system (not shown in FIG. 3). The computer system is configured to calculate an estimated level of liquid in the reservoir based on a difference of the first and second electrical signals output by the differential receiver.

The light output by the first and second optical sources 10a and 10b is guided into the side-emitting optical fiber 4 by way of an optical Y-combiner 32. The optical Y-combiner 32 has two input branches (not shown in FIG. 3) which are respectively optically coupled to the first and second optical sources 10a and 10b by respective optical fibers 30a and 30b. The optical Y-combiner 32 has an output branch (not shown in FIG. 3) which is optically coupled to the side-emitting optical fiber 4 by an optical fiber 34. Each of the optical fibers 10a, 10b and 34 may comprise a single length of optical fiber or a plurality of lengths of optical fiber connected in series by optical connectors (not shown in the drawings). A portion of the light that enters the upper end of the side-emitting optical fiber 4 is emitted toward the side-receiving optical fiber 6. A portion of the light that enters the side-receiving optical fiber 6 exits the upper end of the side-receiving optical fiber 6. The light output by the side-receiving optical fiber 6 is guided into the first and second optical detectors 28a and 28b by way of an optical Y-splitter 38. The optical Y-splitter 38 has an input branch (not shown in FIG. 3) which is optically coupled to the side-receiving optical fiber 6 by an optical fiber 36. The optical Y-splitter 38 has two output branches which are respectively optically coupled to the first and second optical filters 26a and 26b by respective optical fibers 40a and 40b.

Each of the optical fibers 36, 40a and 40b may comprise a single length of optical fiber or a plurality of lengths of optical fiber connected in series by optical connectors (not shown in the drawings).

In the design shown in FIG. 3, if acrylic plastic optical fiber is selected, visible wavelengths (e.g., red, green, blue etc.) have less attenuation than infrared and should be chosen. If glass fiber or perfluorinated plastic fiber is selected, invisible infrared wavelengths have less attenuation and should be chosen. The two wavelengths should be chosen such that they have high contrast of absorption in fuel to give a high optical power ratio for the respective first and second optical detectors 28a and 28b. Since the light beam comprising the first wavelength and the light beam comprising the second wavelength light propagate through the same optical path (assuming that optical fibers 30a and 30b are identical and that optical fibers 40a and 40b are identical), all common-mode intensity variation effects (described hereinabove) that create error in the received power can be neutralized. Only the fuel level in the meniscus tube 8 that modulates the optical signal between the side-emitting and side-receiving optical fibers results in changes to the light that impinges respectively on the first and second optical detectors 28a and 28b. The cladding of the side-emitting optical fiber 4 is modified to enable a controlled level of light output along the fiber's length. The side-receiving optical fiber 6 can be fabricated the same way or can be a fluorescent optical fiber that collects light along the length of the fiber and transmits other light having a different wavelength to the upper end of the side-receiving optical fiber 6. Each bottom end of the side-emitting and side-receiving optical fibers can be fitted with a mirror 18 (see FIG. 9) to reduce the optical power loss out that fiber end.

Fluorescence is the emission of light by a substance that has absorbed light or other electromagnetic radiation. As used herein, the term "fluorescent optical fiber" means an optical fiber that comprises a core surrounded by cladding, wherein the core is doped with special materials that will produce light (i.e., photons) having a first spectral bandwidth centered at a first wavelength when light having a second spectral bandwidth centered at a second wavelength different than the first wavelength is absorbed by that core. Typically the first wavelength is greater than the second wavelength. In accordance with alternative embodiments, fluorescent glass optical fibers can be used instead of fluorescent plastic optical fiber.

Figure 4:
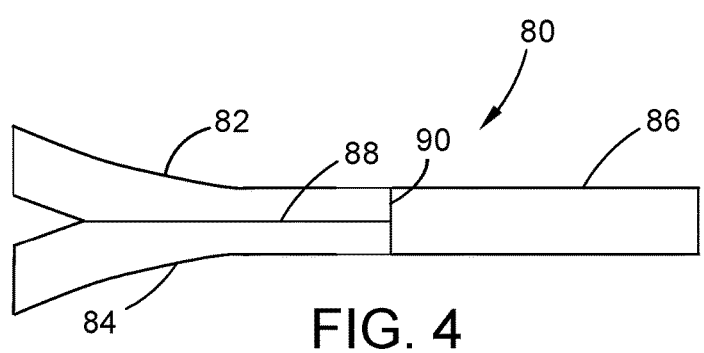
FIG. 4 is a diagram representing a top view of an optical Y-coupler in accordance with one embodiment, which optical Y-coupler may be used as either a combiner or a splitter depending on the direction of the light propagating therethrough.

FIG. 4 is a diagram representing a top view of an optical Y-coupler 80 in accordance with one embodiment. The optical Y-coupler 80 comprises three optical fibers 82, 84 and 86. Although not visible in FIG. 4, the end faces of optical fibers 82 and 84 will be bonded and optically coupled to one end face of optical fiber 86. The optical Y-coupler 80 is designed to facilitate the propagation of incoming light by internal reflection.

In accordance with one proposed implementation, the optical fibers 82, 84 and 56 are made of plastic and have a diameter of 1 mm except along respective end sections of optical fibers 82 and 84. Each of the optical fibers 82 and 84 comprise respective end sections where fiber material has been removed to form respective planar faces and respective semicircular end faces. The end sections begin where the circular cross sections of optical fibers 82 and 84 transition to non-circular and terminate at the respective semicircular end faces. More specifically, the end section of optical fiber 82 is shaped to form a first side face that intersects and is perpendicular to the semicircular end face of optical fiber 82, while the end section of plastic optical fiber 84 is shaped to form a second side face that intersects and is perpendicular to the semicircular end face of optical fiber 84. These side faces are bonded and optically coupled to each other by a first layer of index matching epoxy 88. The semicircular end faces of the optical fibers 82 and 84 combine to form a circular end face that is bonded and optically coupled to a circular end face of the optical fiber 86 by a second layer of index matching epoxy 90, which eliminates back reflection.

The optical Y-combiner 32 and optical Y-splitter 38 (see FIG. 3) may each be constructed as shown in FIG. 4. When optical Y-coupler 80 is being used as a combiner, it guides any light that enters plastic fibers 82 and 84 from the left-hand side (as viewed in FIG. 4) into, through and out of the plastic fiber 86, thereby combining the light from two optical sources. Conversely, when optical Y-coupler 80 is being used as a splitter, it guides any light that enters plastic fiber 86 from the right-hand side (as viewed in FIG. 4) into, through and out of the plastic fibers 82 and 84, thereby splitting the light from the side-receiving optical fiber.

Figure 5:
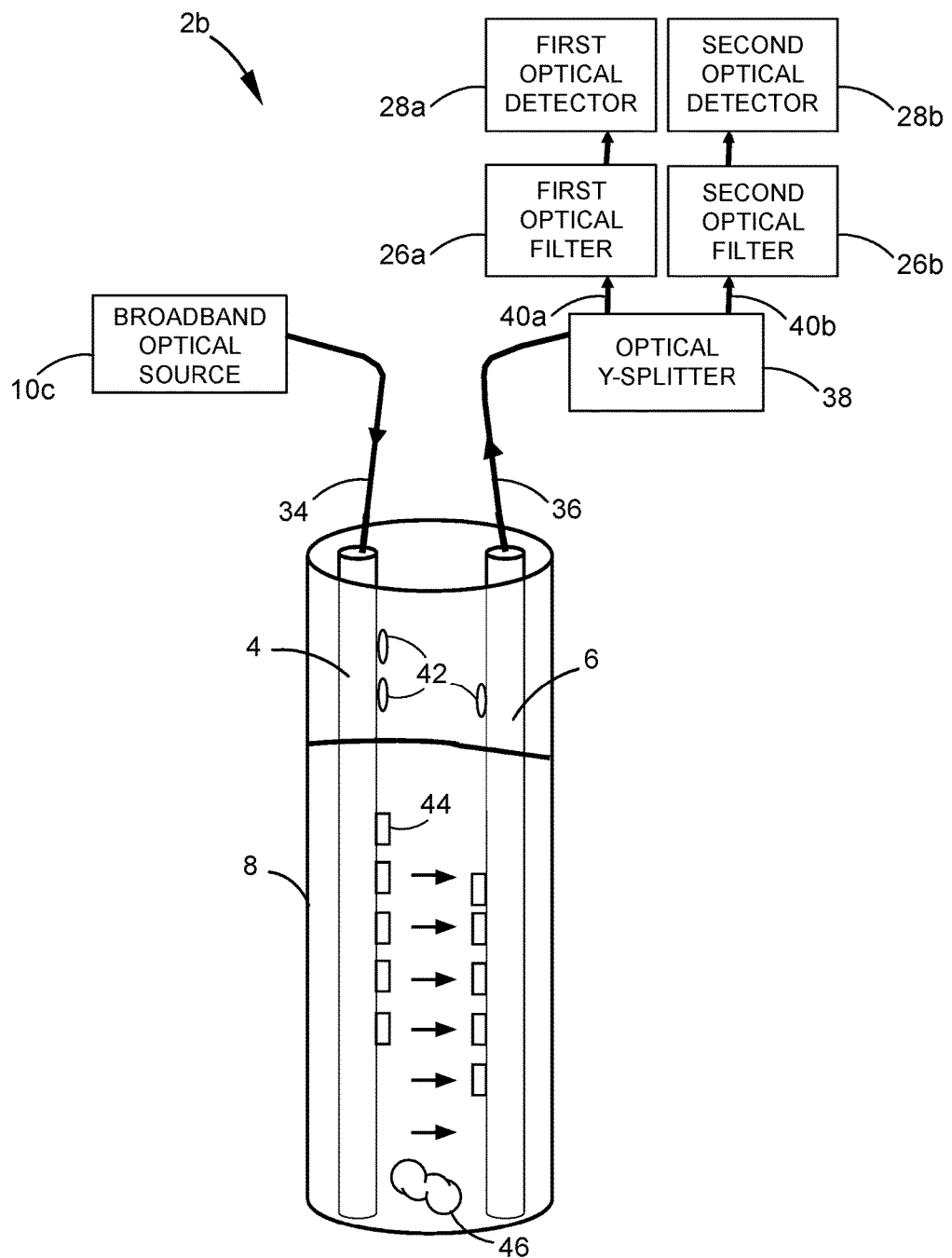
FIG. 5 is a hybrid diagram representing some components of a differential spectral liquid level sensor comprising a broadband optical source and a pair of differential optical detectors in accordance with a second embodiment.

In accordance with a second example embodiment, instead of two different light sources employing an optical Y-coupler or a dichroic mirror, a single broadband light source can be used such as a white LED or RGB LED for visible wavelengths, or a BLED (broadband LED) for infra-red wavelengths. Multiple wavelengths are contained within the broadband light source and the two differential wavelengths will be filtered out for use by two optical detectors with associated wavelength filters. FIG. 5 is a hybrid diagram representing some components of a differential spectral liquid level sensor 2b in accordance with the second example embodiment comprising at least the following components: a broadband optical source 10c that outputs light comprising a bandwidth that encompasses first and second wavelengths; a side-emitting optical fiber 4 that is optically coupled to the broadband optical source 10c; a first optical filter 26a that passes light having the first wavelength, but does not pass light having the second wavelength; a first optical detector 28a that receives light that has passed through the first optical filter 26a; a second optical filter 26b that passes light having the second wavelength, but does not pass light having the first wavelength; a second optical detector 28b that receives light that has passed through the second optical filter 26b; and a side-receiving optical fiber 6 that is optically coupled to the first and second optical detectors by way of the first and second optical filters respectively. The light output by the broadband optical source 10c is guided into the side-emitting optical fiber 4 by way of an optical fiber 34. A portion of the light that enters the upper end of the side-emitting optical fiber 4 is emitted toward the side-receiving optical fiber 6. A portion of the light that enters the side-receiving optical fiber 6 exits the upper end of the side-receiving optical fiber 6. The light output by the side-receiving optical fiber 6 is guided into the first and second optical detectors 28a and 28b by way of an optical Y-splitter 38. The optical Y-splitter 38 has an input branch (not shown in FIG. 5) which is optically coupled to the side-receiving optical fiber 6 by an optical fiber 36. The optical Y-splitter 38 has two output branches which are respectively optically coupled to the first and second optical filters 26a and 26b by respective optical fibers 40a and 40b. The first and second optical detectors 28a and 28b convert impinging light into electrical signals which are sent to a computer system for processing.

Instead of using an optical Y-splitter 38 and a pair of optical filters 26a and 26b to split the optical signals exiting the upper end of the side-receiving optical fiber 6 as shown in FIGS. 3 and 5, other types of optical devices can be used.

Figure 8:
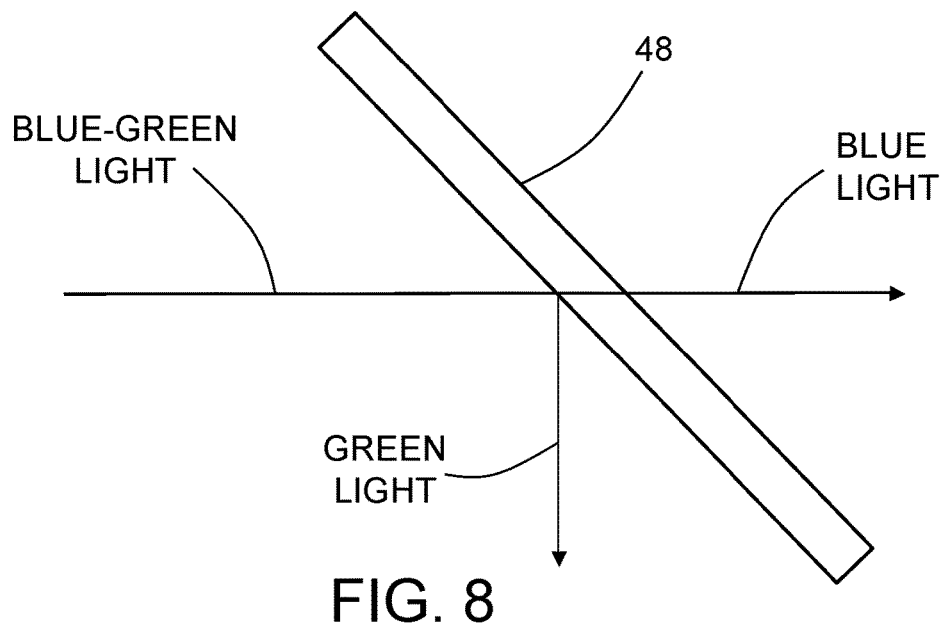
FIG. 8 is a diagram representing a top view of a dichroic mirror which can be used as a beam splitter in place of the optical Y-coupler depicted in FIG. 4.

For example, FIG. 8 shows the equivalent functionality of a dichroic mirror 48. The dichroic mirror 48 has a coating that allows light having a first wavelength (e.g., blue light) to go through and reflects light having a second wavelength different than the first wavelength (e.g., green light). The light of first wavelength would pass through the dichroic mirror 48 and onto the first optical detector 28a, while the light of second wavelength would be reflected by the dichroic mirror 48 onto the second optical detector 28b. The dichroic mirror 48 and the first and second optical filters 26a and 26b form a differential receiver.

In accordance with a third example embodiment, instead of two different wavelength filters and two optical detectors, a single optical detector is used for receiving both wavelengths from two light sources that are time-division multiplexed onto the same optical fiber. On the receive side, the time-division multiplexed optical signals are demultiplexed by means of synchronized switches to allow the respective optical power signals due to the respective wavelengths to be extracted and separately processed by a computer system. The ratio of those separate optical powers can then be calculated, which ratio is indicative of the fuel level in a properly calibrated system.

Figure 6:
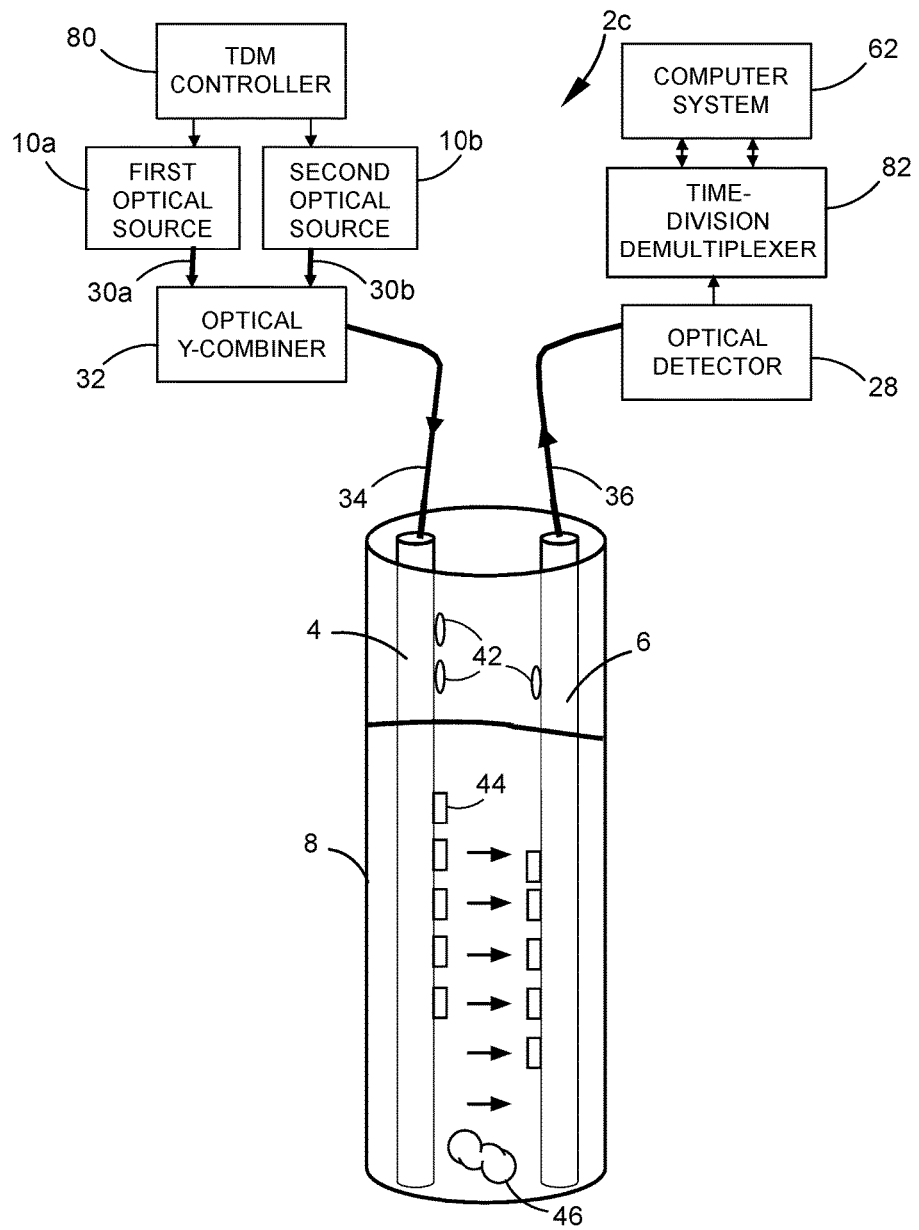
FIG. 6 is a hybrid diagram representing some components of a differential spectral liquid level sensor comprising a pair of differential optical sources and an optical detector in accordance with a third embodiment.

FIG. 6 is a hybrid diagram representing some components of a differential spectral liquid level sensor 2c in accordance with a third example embodiment comprising at least the following components: a first optical source 10a that outputs light comprising a first wavelength; a second optical source 10b that outputs light comprising a second wavelength different than the first wavelength; a time-division multiplexing (TDM) controller 80 configured to control the first and second optical sources 10a and 10b to output time-division multiplexed optical pulses having the first and second wavelengths in alternating sequence; a side-emitting optical fiber 4 that is optically coupled to the first and second optical sources 10a and 10b; a side-receiving optical fiber 6 that is positioned parallel to and at a distance from the side-emitting optical fiber 4; an optical detector 28 that is optically coupled to receive light from the side-receiving optical fiber 6; and a time-division demultiplexer 82 that is electrically coupled to the optical detector 28 and comprises switches which are controlled to demultiplex the time-division-multiplexed optical signals output from the side-receiving optical fiber 6. The fuel level measurement system further comprises a computer system 62 configured to calculate an estimated level of fuel in the fuel tank based on a difference of the demultiplexed signals output from the time-division demultiplexer 82.

Each optical source may comprise an LED and an LED driver that receives control signals from the TDM controller 80. The respective time-division-multiplexed optical pulses output by the first and second optical sources 10a and 10b are guided into the side-emitting optical fiber 4 by way of an optical Y-combiner 32. The optical Y-combiner 32 has two input branches (not shown in FIG. 3) which are respectively optically coupled to the first and second optical sources 10a and 10b by respective optical fibers 30a and 30b. The optical Y-combiner 32 has an output branch (not shown in FIG. 3) which is optically coupled to the side-emitting optical fiber 4 by an optical fiber 34. A portion of the light that enters the upper end of the side-emitting optical fiber 4 is emitted toward the side-receiving optical fiber 6. A portion of the light that enters the side-receiving optical fiber 6 exits the upper end of the side-receiving optical fiber 6. The light output by the side-receiving optical fiber 6 is guided into the optical detector 28 by way of an optical fiber 36. The optical detector 28 converts impinging optical pulses into electrical signals which are sent to the time-division demultiplexer 82.

Figure 7:
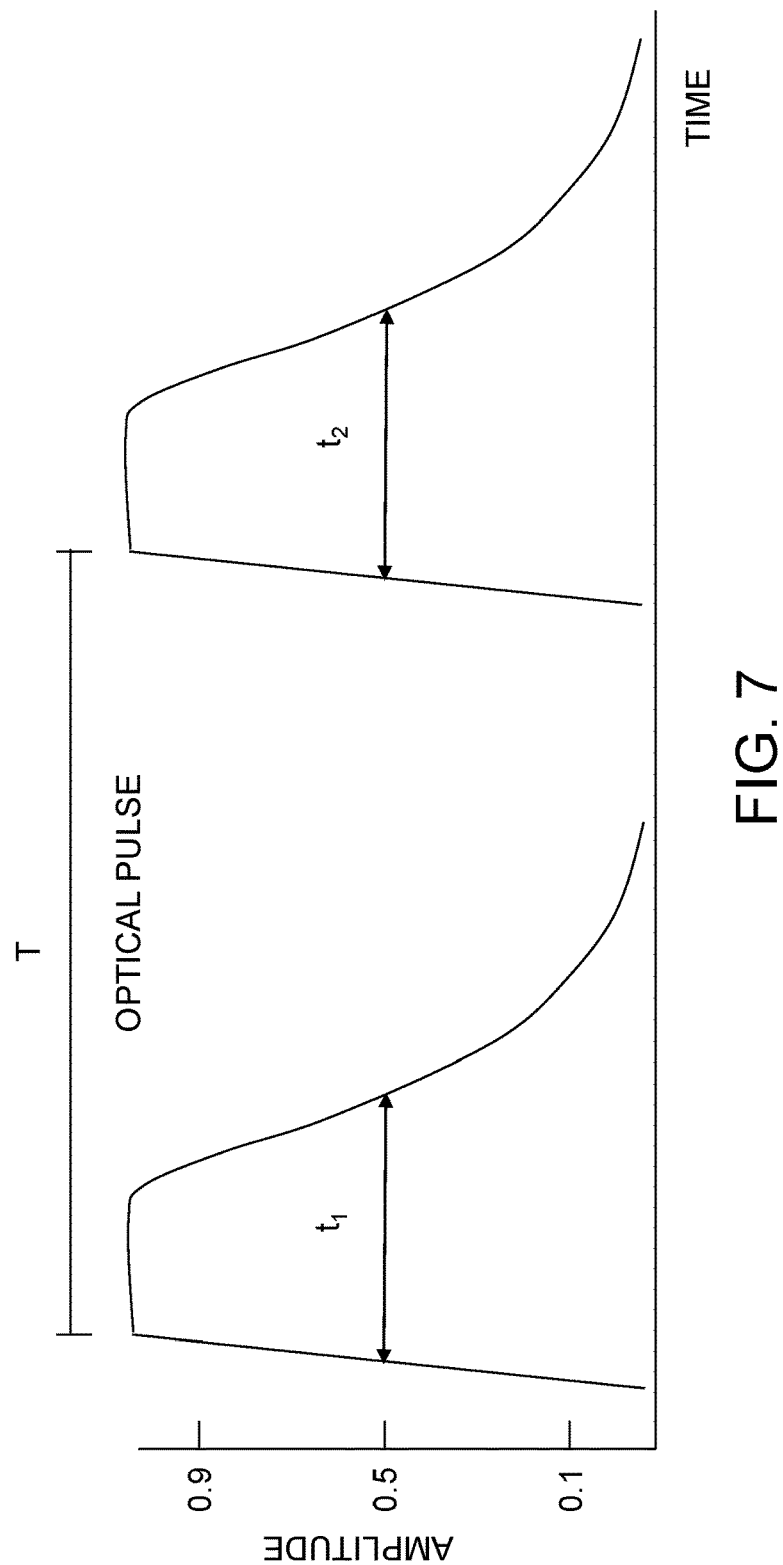
FIG. 7 is a graph showing two optical pulses in accordance with a time-division-multiplexing scheme used in the third embodiment partly depicted in FIG. 6. The vertical axis measures optical pulse amplitude; the horizontal axis measures time.

FIG. 7 is a graph showing two optical pulses in accordance with a time-division multiplexing scheme used in the third example embodiment partly depicted in FIG. 6. The vertical axis measures optical pulse amplitude; the horizontal axis measures time. The optical pulse widths $t_1$ and $t_2$, as well as the period of each pulse train and time interval T between the two different color optical pulses, can be chosen to optimize the response for each wavelength and for the power ratio of the two optical signals. To improve linearization response in fuel, the optical sources can be driven with a current signal waveform having an exponential falling edge, corresponding to the exponential attenuation of optical power as the emitted light propagates through the fuel column.

Figure 9:
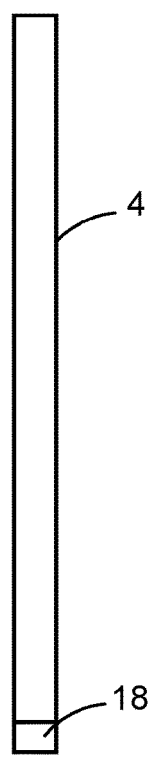
FIG. 9 is a diagram representing an elevation view of an optical fiber having a mirror cap at one end for increasing the intensity of light inside the fiber.

As shown in FIG. 9, a reflective mirror cap 18 may be attached to the bottom end of the side-emitting optical fiber 4 to reflect light back through side-emitting optical fiber 4 and to prevent light from being lost out the bottom end. A similar reflective cap may be attached to the bottom end of the side-receiving optical fiber 6 to reflect light back through the side-receiving optical fiber 6 toward the optical detector 14 (see FIG. 3).

Figure 10:
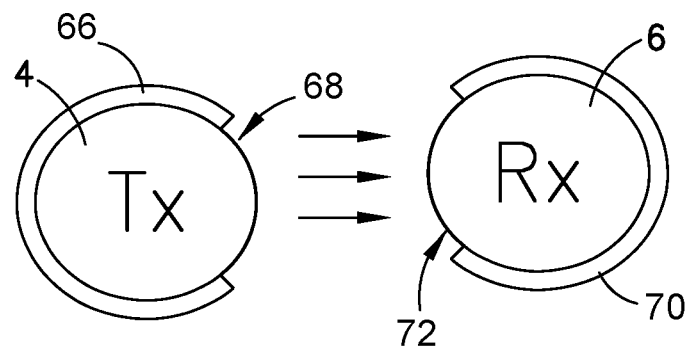
FIG. 10 is a diagram representing a plan view of a pair of optical fibers encased in respective jackets having mutually opposing longitudinal slots for sideways optical coupling of light (indicated by arrows) from the side-emitting optical fiber to the side-receiving optical fiber.

FIG. 10 is a diagram representing a plan view of a pair of straight light guides of an optical sensor in accordance with an embodiment intended for use in the measurement of a level of a liquid that will not damage exposed optical fibers when the latter are immersed in the liquid. The transmitting light guide comprises: a side-emitting optical fiber 4 having an axis and a circumferential surface; and a jacket 66 having a longitudinal slot 68 that extends parallel to the axis of the side-emitting optical fiber 4 for the entire length of the latter. Preferably the longitudinal slot 68 overlaps a side window formed by a non-uniform surface on the cladding of the side-emitting optical fiber 4. The jacket 66 is in contact with and covers the circumferential surface of the side-emitting optical fiber 4 except in the area of longitudinal slot 68. The transmitting light guide may further comprise a curved reflective surface disposed between the side-emitting optical fiber 4 and the jacket 66. Preferably the jacket 66 is made of a material which is not optically transparent or translucent, such as metal or polymeric material.

Similarly, the receiving waveguide comprises: a side-receiving optical fiber 6 having an axis and a circumferential surface; and a jacket 70 having a longitudinal slot 72 that extends parallel to the axis of the side-receiving optical fiber 6 for the entire length of the latter. Preferably the longitudinal slot 72 overlaps the side window formed by a non-uniform surface on the cladding of the side-receiving optical fiber 6. The jacket 70 is in contact with the circumferential surface of the side-receiving optical fiber 6 except in an area of the longitudinal slot 72. The receiving waveguide may further comprise a curved reflective surface disposed between the side-receiving optical fiber 6 and the jacket 70. Preferably the jacket 70 is made of a material which is not optically transparent or translucent, such as metal or polymeric material.

In the case where the jackets 66 and 70 are made of polymeric material, those jackets can be formed by molding. The side-emitting and side-receiving optical fibers may each have a circular, square or hexagonal cross section, with the molded jacket conforming to the shape of the optical fiber.

The arrows in FIG. 10 represent light which has been emitted by side-emitting optical fiber 4 through the side window formed in the cladding of the side-emitting optical fiber 4 and is propagating through intervening fluid (e.g., liquid or air) toward the corresponding side window formed in the cladding of side-receiving optical fiber 6. However, it should be appreciated that, in the absence of a focusing lens overlying the side window of the side-emitting optical fiber 4, the exiting rays of light may be divergent, rather than collimated.

Figure 11:
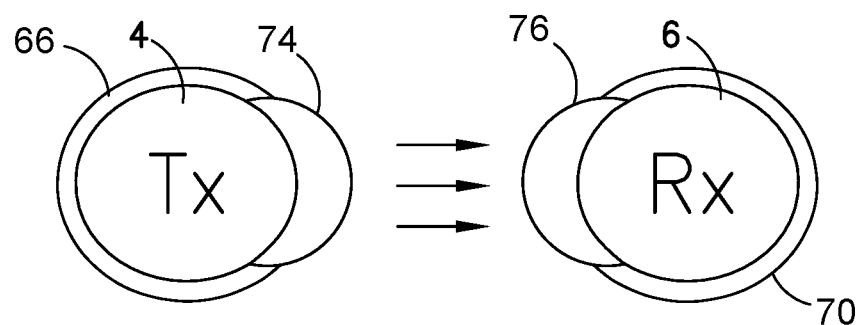
FIG. 11 is a diagram representing a plan view of a pair of optical fibers encased in respective jackets having mutually opposing longitudinal slots covered by respective lenses for sideways optical coupling of light (indicated by arrows) from the side-emitting optical fiber to the side-receiving optical fiber.

FIG. 11 is a diagram representing a plan view of a pair of straight light guides of an optical sensor in accordance with an embodiment in which the liquid is not in direct contact with the side-emitting and side-receiving optical fibers 4 and 6. The only difference from the embodiment depicted in FIG. 10 is that the transmitting and receiving light guides further comprise respective lenses 74 and 76 formed (e.g., by molding) in the longitudinal slots of the respective jackets 66 and 70. Preferably the lenses 74 and 76 extend the full length of the longitudinal slots. In combination, lens 74 and jacket 66 encase the side-emitting optical fiber 4, with lens 74 interfacing with the side window of side-emitting optical fiber 4. Similarly, lens 76 and jacket 70 encase the side-receiving optical fiber 6, with lens 76 interfacing with the side window of side-receiving optical fiber 6. Preferably the lenses 74 and 76 are made of epoxy.

The arrows in FIG. 11 represent light which has been emitted by side-emitting optical fiber 4 through the lens 74 and is propagating through intervening fluid (e.g., liquid or air) toward the lens 76 of the receiving light guide. The lens 74 may be designed so that exiting rays of light are directed in parallel toward the lens 76. The lens 76 may be designed so that impinging parallel rays of light are converged into the side-receiving optical fiber 6. The lenses have the effect of increasing the intensity of the light output by side-receiving optical fiber 6 for the same optical power being pumped into side-emitting optical fiber 4, thereby enhancing the performance of the optical impedance sensor.

If the optical power transmitted by a high-intensity LED is adequate, then the system may comprise a single side-emitting optical fiber disposed parallel with one side-receiving optical fiber. If the optical power from one LED is inadequate, then the amount of light emitted can be increased in various ways. In some embodiments, the system may comprise two or more side-emitting optical fibers surrounding a centrally located side-receiving optical fiber. In this case the side-receiving optical fiber is collecting light from all sides, and each side-emitting optical fiber has its own set of differential optical sources. In these alternative embodiments, the signal-to-noise ratio of the optical impedance sensor is increased by employing multiple side-emitting and/or side-receiving optical fibers.

Any one of the above-described fuel level sensors may be installed in a fuel tank onboard an airplane along with a temperature sensor and a densitometer. The fuel level and fuel density data and geometry of the fuel tank can then be used to compute the estimated quantity (i.e., mass) of fuel in the fuel tank. (In order to measure the mass of the fuel for engine consumption and range calculation, the system can use measurements of fuel level and fuel density.) In addition, an airplane can be retrofit by removing existing electrical fuel level sensors and installing optical fuel level sensors in their place. In accordance with one fuel level sensor configuration, the locations of the respective sensors in the wing tank and the center tank of an airplane dictate the sensor height and therefore fiber sensor length. In the baseline configuration there would be a one-to-one replacement of each electrical sensor by an optical sensor. The double-shielded electrical wiring for the electrical sensor will be replaced by lightweight optical fiber, eliminating weight from the wiring and supporting brackets, and eliminating electromagnetic effects from lightning, shorting, fraying of electrical wiring. The use of optical fibers instead of electrical wires also eliminates any safety hazards due to electrical fault conditions. Although glass fiber can be used, plastic optical fiber is more flexible and more forgiving for installation in the very tight space of an airplane fuel tank.

Figure 12:
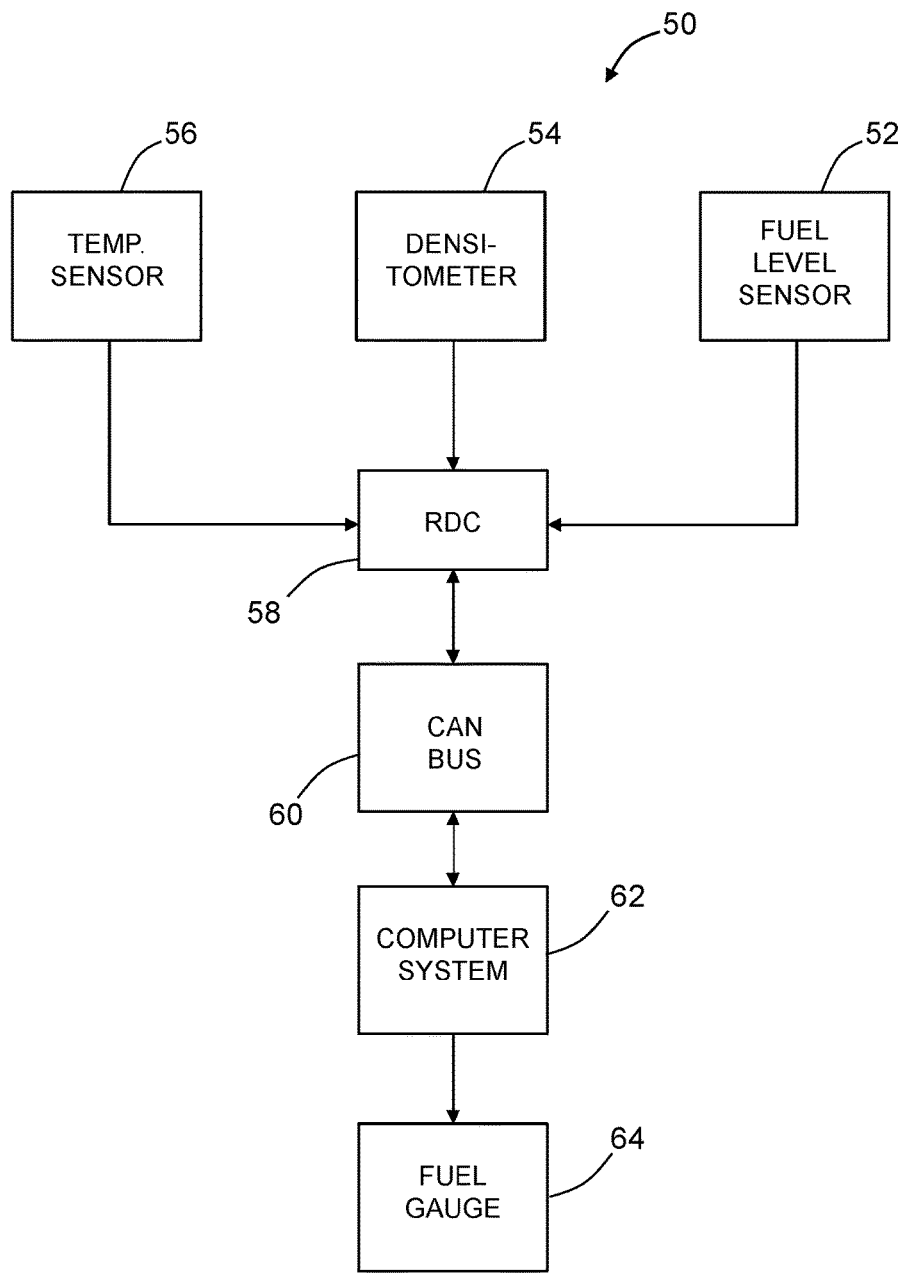
FIG. 12 is a block diagram identifying some components of a system for providing a pilot with an indication of the estimated quantity of fuel remaining in the fuel tanks.

FIG. 12 is a block diagram representing components of a system for measuring a quantity of fuel in a fuel tank in accordance with one embodiment. The system comprises a fuel level sensor 52 (of a type described above) that outputs electrical signals representing the level of fuel in a fuel tank, a densitometer 54 that outputs electrical signals representing the density of the fuel in the fuel tank and a temperature sensor 56 that outputs electrical signals representing the temperature of the fuel in the fuel tank. Each of these sensors may be incorporated in a respective line replaceable unit (LRU). These LRUs are connected to a remote data concentrator (RDC) 58.

In accordance with one implementation, the RDC 58 is connected to a computer system 62 (e.g., a fuel quantity processing unit) by way of a multi-master serial bus known as a CAN bus 60. For this purpose, the RDC 58 and the computer system 62 may each incorporate a controller and a transceiver of the type used in a controller area network (CAN). Such a CAN controller and CAN transceiver are referred to herein as a "CAN node". The RDC 58 has different dedicated analog circuits to separately measure the temperature, density, and level of the fuel. The analog values of these parameters are converted to digital values, packed in a data field and transmitted via the CAN bus 60 to the computer system 62. Note that ARINC 845 CAN bus is just an example of a simple avionic digital data bus that can be used and that any other digital data bus such as ARINC 425 or ARINC 664 can be used as well.

In accordance with the CAN communications protocol, each CAN node is able to send and receive messages, but not simultaneously. A message or frame consists primarily of an identifier, which represents the priority of the message, and a number of data bytes. The message is transmitted serially onto the CAN bus 60 by the CAN transceiver and may be received by all CAN nodes. Each CAN node connected to CAN bus 60 waits for a prescribed period of inactivity before attempting to send a message. If there is a collision (i.e., if two nodes try to send messages at the same time), the collision is resolved through a bit-wise arbitration, based on a preprogrammed priority of each message in the identifier field of the message. The message that contains the highest priority identifier always wins bus access.

The sensor data acquired by fuel level sensor 52, densitometer 54 and temperature sensor 56 is formatted in accordance with the CAN communications protocol to form CAN messages, which are broadcast onto the CAN bus 60 and received by the computer system 62. The computer system 62 is configured to estimate the mass of fuel remaining in the fuel tank (or compartment thereof) based on the measured fuel density, the known geometry of the fuel tank (or compartment thereof) and the measured fuel level h. For example, the volume of fuel remaining can be computed based on the known geometry and measured fuel level, and then the mass of fuel remaining will be equal to the product of volume and density. An electrical signal representing the estimated mass of remaining fuel is output from the computer system 62 to a fuel gauge 64. The fuel gauge 64 may take the form of a display device having a display processor programmed to display the measurement results (e.g., the fuel level or the fuel quantity) graphically and/or alphanumerically on a display screen.

In accordance with one proposed implementation, a differential spectral fuel level sensor is installed in a compartment of a fuel tank. Each optical source is in the form of a transmit integrated circuit connected to a transmit optical subassembly (comprising a laser or LED). Each optical detector is in the form of a receive integrated circuit connected to a receive optical subassembly (comprising a photodiode). The magnitude of the fuel level signals output by the differential spectral fuel level sensor increases monotonically with increasing intensity of light emitted from the end of the side-receiving optical fiber 6. The computer system 62 may be a dedicated microprocessor or a general-purpose computer configured to perform differential processing of signals representing the respective optical powers for the respective first and second wavelengths. This differential processing removes the undesirable effects of any common-mode intensity variations. The results of the differential processing are then used to calculate the measured level (i.e., height) of the fuel by using a look-up table, a calibration curve, or by solving equations, as appropriate.

The computer system 62 may be a computer or part of a flight control system located on an aircraft. In identifying the amount of fuel present in an irregular-shaped fuel tank, the computer system 62 may execute various routines to calculate the amount of fuel present based on optical power data received from multiple side-receiving optical fibers appropriately placed in various compartments of the fuel tank. The fuel information processing software may include routines that take into account the shape of the fuel tank to determine the amount of fuel remaining in the fuel tank. The fuel information processing software may further include routines for calibrating processes to form a baseline before a first use or to maintain accuracy of fuel readings. The readings provided by the computer system 62 to the fuel gauge 64 may be integrated or averaged before presentation and may be provided at different time intervals.

While optical fuel level sensors have been described with reference to various embodiments, it will be understood by those skilled in the art that various changes may be made and equivalents may be substituted for elements thereof without departing from the teachings herein. In addition, many modifications may be made to adapt the concepts and reductions to practice disclosed herein to a particular situation. Accordingly, it is intended that the subject matter covered by the claims not be limited to the disclosed embodiments.

The embodiments disclosed above use one or more computing systems. As used in the claims, the term "computing system" comprises one or more of the following: a computer, a processor, a controller, a central processing unit, a microcontroller, a reduced instruction set computer processor, an ASIC, a programmable logic circuit, an FPGA, a digital signal processor, and/or any other circuit or processing device capable of executing the functions described herein. For example, a computing system may comprise multiple microcontrollers or multiple processors which communicate via a network or bus. As used herein, the terms "computer" and "processor" both refer to devices having a processing unit (e.g., a central processing unit) and some form of memory (i.e., computer-readable medium) for storing a program which is readable by the processing unit.

The methods described herein may be encoded as executable instructions embodied in a non-transitory tangible computer-readable storage medium, including, without limitation, a storage device and/or a memory device. Such instructions, when executed by a processing or computing system, cause the system device to perform at least a portion of the methods described herein.

The process claims set forth hereinafter should not be construed to require that the steps recited therein be performed in alphabetical order (any alphabetical ordering in the claims is used solely for the purpose of referencing previously recited steps) or in the order in which they are recited unless the claim language explicitly specifies or states conditions indicating a particular order in which some or all of those steps are performed. Nor should the process claims be construed to exclude any portions of two or more steps being performed concurrently or alternatingly unless the claim language explicitly states a condition that precludes such an interpretation.

The invention claimed is:

1. A system for measuring a level of liquid in a reservoir, comprising:
    one optical source which alone or two optical sources which collectively outputs light having a first wavelength and light having a second wavelength different than the first wavelength;
    a side-emitting optical fiber optically coupled to the one or two optical source(s);
    a side-receiving optical fiber that is positioned parallel to and at a distance from the side-emitting optical fiber;
    a differential receiver optically coupled to the side-receiving optical fiber and configured to convert light having the first wavelength into first electrical signals and convert light having the second wavelength into second electrical signals, wherein the differential receiver comprises:
    a first optical filter that passes light having the first wavelength, but does not pass light having the second wavelength;
    a second optical filter that passes light having the second wavelength, but does not pass light having the first wavelength;
    a first optical detector arranged to detect light that has passed through the first optical filter and output first electrical signals representing an amount of detected light having the first wavelength;
    a second optical detector arranged to detect light that has passed through the second optical filter and output second electrical signals representing an amount of detected light having the second wavelength; and
    a computer system configured to calculate an estimated level of liquid in the reservoir based on a ratio of the first and second electrical signals output by the first and second optical detectors.

2. The system as recited in claim 1, further comprising a display device electrically coupled to the computing system, wherein the computing system is further configured to execute the following operations:
    storing data representing a geometry of the reservoir;
    receiving data representing a measurement of a density of the liquid in the reservoir;
    calculating a mass of liquid remaining in the reservoir based on the geometry of the reservoir, the density of the liquid and the estimated level of liquid; and
    outputting an electrical signal representing the calculated mass of liquid in the reservoir to the display device.

3. The system as recited in claim 1, wherein the light comprising a first wavelength and the light comprising a second wavelength have different attenuations when propagating through the liquid.

4. The system as recited in claim 1, further comprising an optical Y-combiner having first and second input branches optically coupled to the first and second optical sources respectively and an output branch optically coupled to the side-emitting optical fiber.

5. The system as recited in claim 1, further comprising an optical Y-splitter having an input branch optically coupled to the side-receiving optical fiber and first and second output branches optically coupled to the first and second optical detectors by way of the first and second optical filters respectively.

6. The system as recited in claim 1, further comprising a meniscus tube surrounding the side-emitting optical fiber and the side-receiving optical fiber.

7. A method for measuring a height of liquid in a reservoir, comprising:
   placing a side-emitting optical fiber and a side-receiving optical fiber in the reservoir having respective locations whereat the side-emitting optical fiber and side-receiving optical fiber are mutually parallel and separated by a distance;
   outputting light having a first wavelength and light having a second wavelength different than the first wavelength from a single broadband optical source or from respective optical sources, wherein the light having a first wavelength and the light having a second wavelength have different attenuations when propagating through the liquid;
   guiding the outputted light having the first and second wavelengths into the side-emitting optical fiber;
   side-emitting at least some of the light received by the side-emitting optical fiber toward the side-receiving optical fiber;
   guiding at least some of the light received by the side-receiving optical fiber onto a first optical filter;
   guiding at least some of the light received by the side-receiving optical fiber onto a second optical filter;
   converting light having the first wavelength that passes through the first optical filter into first electrical signals representing an amount of detected light having the first wavelength;
   converting light having the second wavelength that passes through the second optical filter into second electrical signals representing an amount of detected light having the second wavelength; and
   calculating an estimated level of liquid in the reservoir based on a ratio of the first and second electrical signals.

8. The method as recited in claim 7, further comprising:
   storing data representing a geometry of the reservoir;
   measuring a density of the liquid in the reservoir;
   calculating a mass of liquid remaining in the reservoir based on the geometry of the reservoir, the density of the liquid and the estimated level of liquid; and
   displaying a gauge that indicates the calculated mass of liquid in the reservoir.

9. The method as recited in claim 7, wherein the liquid is fuel and the reservoir is a fuel tank onboard an airplane.

10. The method as recited in claim 7, wherein guiding light onto the first and second optical filters further comprises splitting the light output by the side-receiving optical fiber.

11. A system for measuring a level of liquid in a reservoir, comprising:
   a first optical source that outputs light having a first wavelength;
   a second optical source that outputs light having a second wavelength different than the first wavelength;
   a side-emitting optical fiber optically coupled to the first and second optical sources;
   a side-receiving optical fiber that is positioned parallel to and at a distance from the side-emitting optical fiber;
   a differential receiver optically coupled to the side-receiving optical fiber and configured to convert light having the first wavelength into first electrical signals and convert light having the second wavelength into second electrical signals, wherein the differential receiver comprises:
   a first optical filter that passes light having the first wavelength, but does not pass light having the second wavelength;
   a second optical filter that passes light having the second wavelength, but does not pass light having the first wavelength;
   a first optical detector arranged to detect light that has passed through the first optical filter and output first electrical signals representing an amount of detected light having the first wavelength;
   a second optical detector arranged to detect light that has passed through the second optical filter and output second electrical signals representing an amount of detected light having the second wavelength; and
   a computer system configured to calculate an estimated level of liquid in the reservoir based on a ratio of the first and second electrical signals output by the first and second optical detectors.

* * * * *